US006682518B1

(12) United States Patent
Rothstein

(10) Patent No.: US 6,682,518 B1
(45) Date of Patent: Jan. 27, 2004

(54) INJECTABLE MICRO-GLASS VIAL

(75) Inventor: Edwin C. Rothstein, Jamesburg, NJ (US)

(73) Assignee: Labtest Associates, Inc., New Brunswick, NJ (US)

( * ) Notice: Subject to any disclaimer, the term of this patent is extended or adjusted under 35 U.S.C. 154(b) by 278 days.

(21) Appl. No.: 09/596,209

(22) Filed: Jun. 16, 2000

(51) Int. Cl.[7] .................................... A61B 19/00
(52) U.S. Cl. .................................... 604/415; 604/411
(58) Field of Search .................................... 604/403, 411, 604/415, 414; 215/247–49, DIG. 3

(56) References Cited

U.S. PATENT DOCUMENTS 4,094,641 A * 6/1978 Friswell ..................... 215/12.1
4,979,630 A * 12/1990 Rose et al. ................. 141/310
5,213,860 A * 5/1993 Laing ......................... 215/253
5,221,311 A * 6/1993 Rising et al. ................. 215/47
5,470,537 A * 11/1995 Siegel ....................... 215/12.1
6,357,489 B1 * 3/2002 Zinger ......................... 141/18

* cited by examiner

*Primary Examiner*—Angela D. Sykes
*Assistant Examiner*—Leslie Deak
(74) *Attorney, Agent, or Firm*—Darby & Darby

(57) ABSTRACT

An improved vial for supplying fluids, such as volatile and toxic fluids, without risking contamination or escape of the fluid before use comprises a sealed glass body containing the fluid. One end of the vial has a weakened area therein of a predetermined thickness which is sufficiently thin that the weakened area can be pierced by a needle without damaging the needle. The vial is be placed in a standard autosampler jar so that the weakened area is adjacent the elastomeric closure. Samples are drawn by plunging a needle through an exposed portion of the closure and into the jar. When the needle is inserted into the jar, it also pierces the weakened area of the vial providing safe access to the fluid contained therein.

20 Claims, 7 Drawing Sheets

INJECTABLE MICRO-GLASS VIAL

FIELD OF THE INVENTION

This invention is directed to a glass vial for storing a fluid and which can be pierced with a needle to permit subsequent removal of the fluid.

BACKGROUND OF THE INVENTION

It is common in many industries, such as laboratory, medical, and photographic, to use volatile and toxic fluids. Often, these fluids are supplied in containers which store a measured quantity of the substance, such as a single unit or dose. A typical container used for these purposes is a glass autosampler jar 10, such as illustrated in FIG. 1. The jar 10 includes a body 12 for containing the fluid and a cap 14. The jar is sealed using an elastomeric closure, such as a rubber septum 18 placed between the cap 14 and the jar's mouth. To permit safe removal of the contained fluid, the cap 14 has an opening 16 in it which exposes the underlying rubber septum 18. The fluid is extracted from the jar by piercing the septum 18 with a hollow needle and drawing the fluid through the needle. Extraction can be performed manually, such as when the jar contains a unit dose of medicine to be injected into a patient by a doctor, or automatically, as when the jars are processed by automated machinery.

Although an elastomeric closure is generally required to provide a secure seal, elastomeric closures are not suitable for use with many types of compounds. In some cases, the fluid compound in the jar can leach through the closure and escape, posing a health risk to the handler. In other instances, the stored compound can cause breakdown in the closure material which can result in escape of the fluid or contamination of the fluid sample itself from chemicals escaping the closure. See, e.g., J. Milano and L. Bailey, "*Evaluation of Current Compendial Physiochemical Test Procedures for Pharmaceutical Elastomeric Closures and Development of an Improved HPLC Procedure*," PDA Journal of Pharmaceutical Science & Technology, Vol. 53, No. 4, p. 202–210 (July 1999).

One solution to this problem is to limit the amount of time the fluid is stored within the needle-piercable jar 10 by filling the jar shortly before it is to be used.

To this end, many volatile and toxic fluids are provided in sealed glass vials 20, such as illustrated in FIG. 2. The vial is filled with the desired fluid 22 and the vial is sealed by melting the glass at the open top. To open the vial 20, the neck 24 is scored using a diamond scribe or other tool to create a weakened area and the top 26 of the vial 20 is snapped off. The fluid is then extracted from the vial 20 and added to the autosampler jar 10, e.g., by pouring the fluid in or transporting it via a syringe or pipette.

Various techniques have been developed to safely remove the top of a sealed vial 20 and then transport the fluids from the vial into the jar 10. However, because in all cases the vial 20 is opened before its contents are placed in the jar 10, the risk of contamination or escape of the fluid is always present. Accordingly, there is a need to provide a method for supplying volatile and toxic fluids in a manner which permits them to be placed in a jar 10 sealed with an elastomeric closure without risking contamination or escape of the fluid or breakdown of the closure.

SUMMARY OF THE INVENTION

An improved vial for supplying fluids, such as volatile and toxic fluids, without risking contamination or escape of the fluid is disclosed. The vial comprises a glass body having a sealed first end and an open second end. The first end has a weakened area therein of a predetermined thickness which is sufficiently thin that the weakened area can be pierced by a needle without damaging the needle. The vial is filled with the desired fluid and then the second end is sealed, e.g., by melting the glass at the second end using a micro-flame.

In use, the vial is placed within a standard autosampler jar such that the weakened first end is adjacent to the elastomeric closure through which samples are to be drawn. An elastic spacer can be placed on the second end of the vial to protect it within the jar and to press the weakened end of the vial upwards against the closure. Samples are drawn in the conventional manner by plunging a needle through an exposed portion of the closure and into the jar. When the needle is inserted into the jar, it also pierces the weakened area of the vial providing safe access to the fluid contained therein.

Advantageously, the fluid contained in the vial remains sealed until the moment when the sample is drawn. This greatly minimizes the likelihood of the sample being contaminated or operators coming into contact with the fluid. In addition, because the closure is not exposed to the fluid until the sample is actually drawn, the fluid (within the sealed vial) can be stored inside the vial for extended periods of time without concern as to whether the fluid will interact detrimentally with the closure.

BRIEF DESCRIPTION OF THE DRAWINGS

The foregoing and other features of the present invention will be more readily apparent from the following detailed description and drawings of illustrative embodiments of the invention in which.

DETAILED DESCRIPTION OF THE PREFERRED EMBODIMENTS

Figure 1:
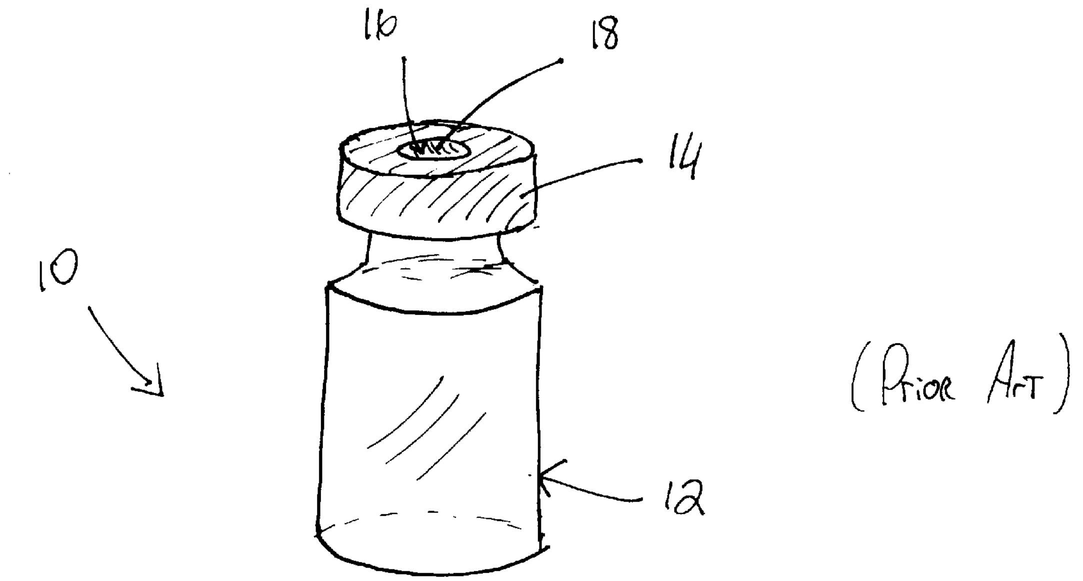
FIG. 1 is an illustration of a conventional autosampler jar.
Figure 2:
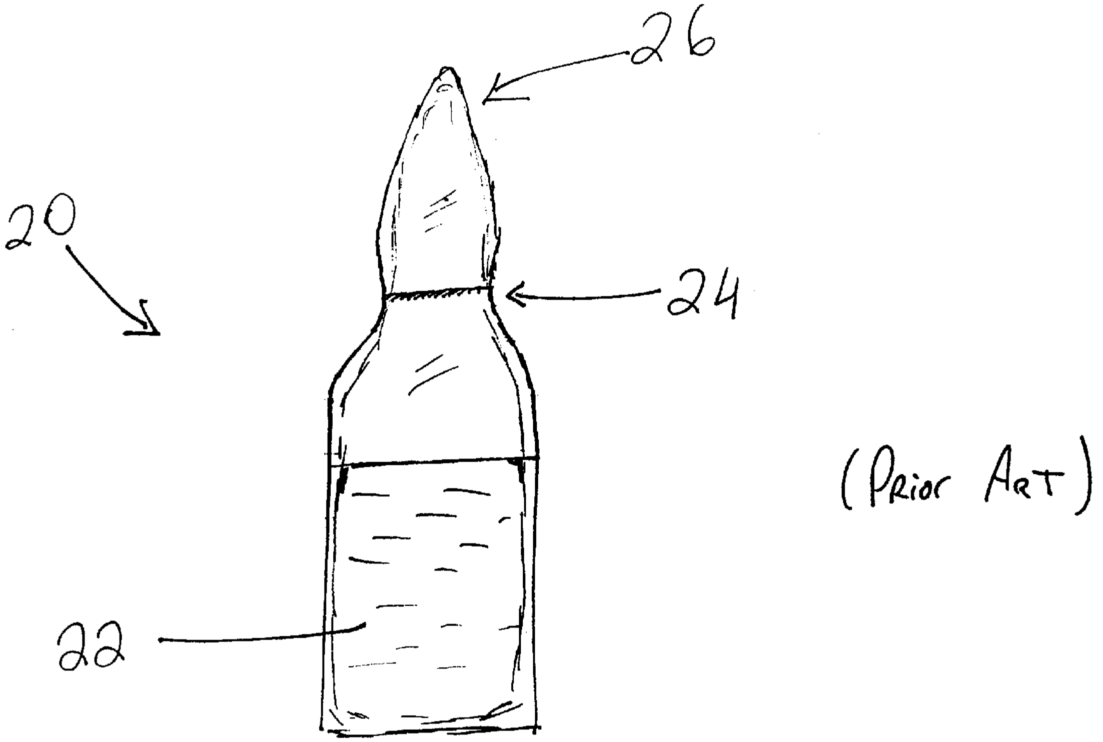
FIG. 2 is an illustration of a conventional sealed glass vial for storing a fluid.
Figure 3A:
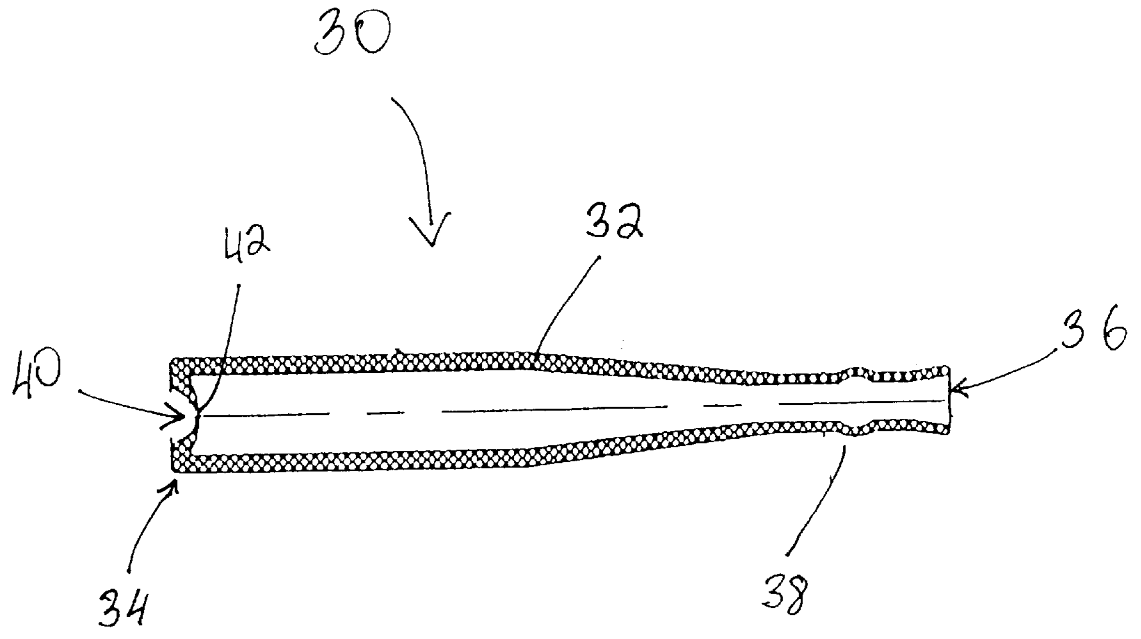
FIGS. 3*a* and 3*b* are side views of an unfilled injectable vial.
Figure 3B:
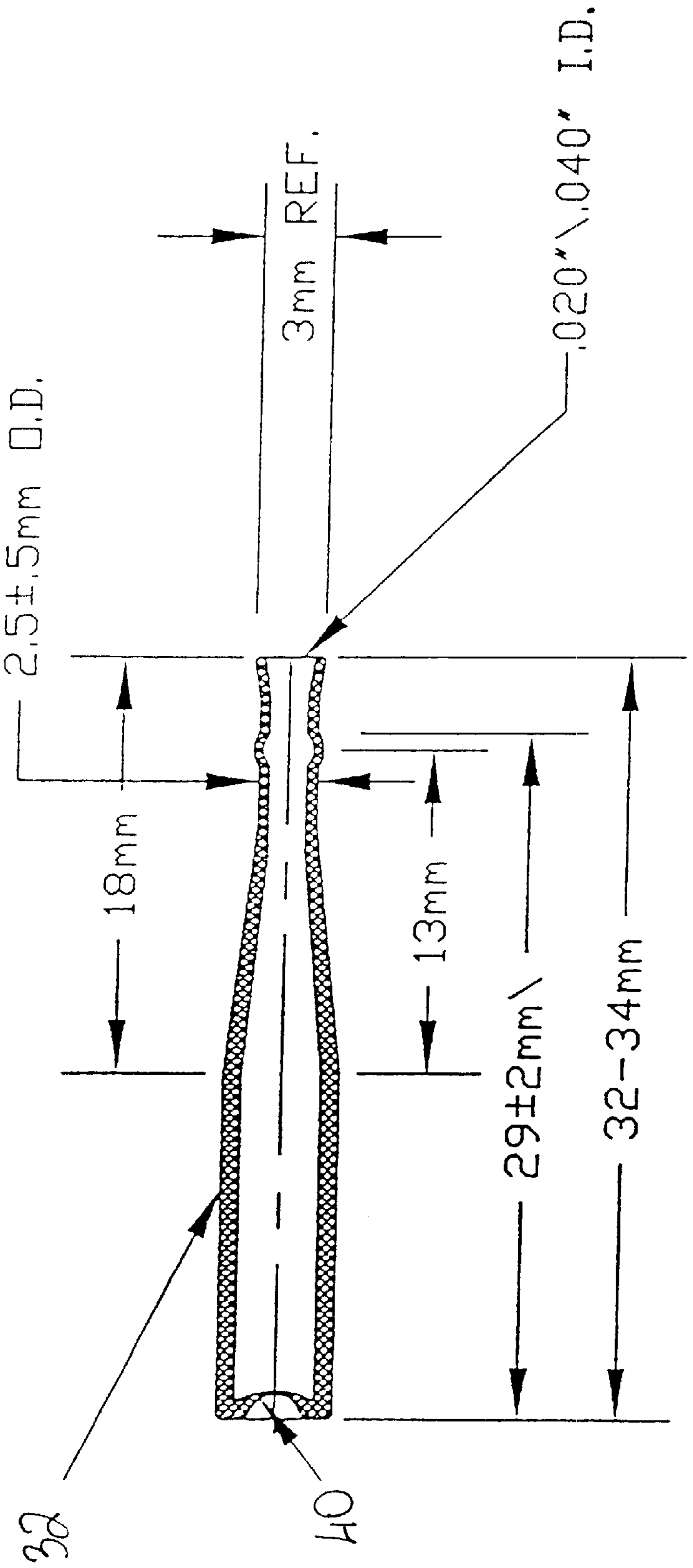

FIGS. 3*a* is a side view of an unfilled injectable vial 30 according to the invention. The vial 30 has a body 32, such as an elongated cylindrical body, which has a first end 34 which is sealed and second end 36 which is open. The vial 30 is preferably made of glass. However, other glass-like or even non-glass substances known to those of skill in the art could be used instead. The specific material used should be able to securely contain and not react with the fluids of interest. The vial 30 can be formed in various configurations and dimensions. FIG. 3*b* shows specific dimensions for a particularly preferred embodiment of the vial 30.

Figure 4:
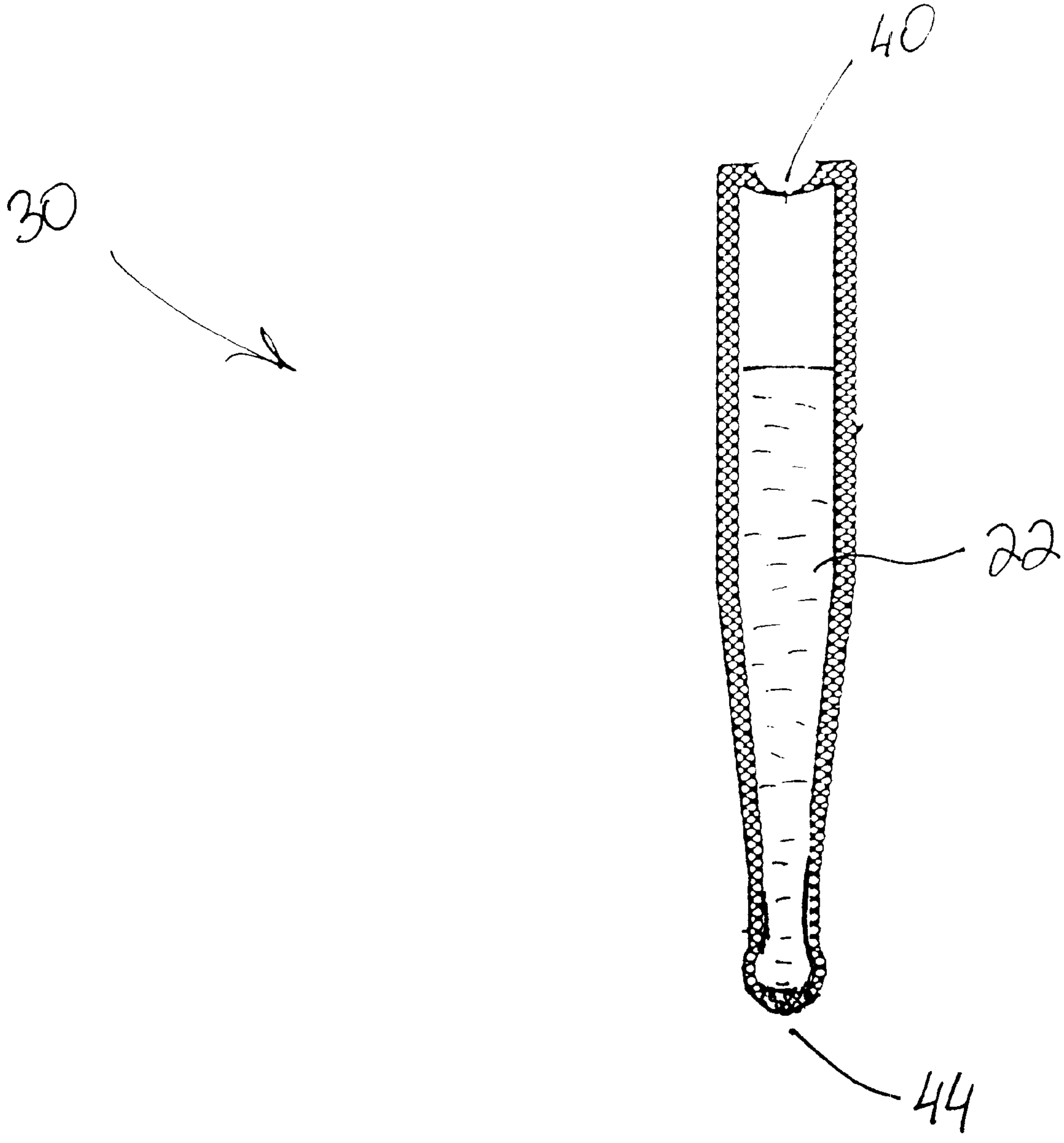
FIG. 4 is a side view of a filled injectable vial.

As shown in FIG. 4, once the vial 30 is filled with the desired fluid 22, the open second end 36 is sealed. The preferred method of sealing the vial 30 is by melting the vial material in the region of the second so that it flows together to form an end-wall 44. If a sufficiently small and hot flame is used, the open end can be sealed without substantial heating of the contained fluid. To aid in the sealing process, a ridge or bubble of material 38 can be formed in the region near the open end 36. Various techniques for sealing glass vials are well known to those of skill in the art.

According to one aspect of the invention, the first end 34 has a weakened area 40 formed therein, at least a portion of which has a predetermined thickness. The predetermined thickness is selected to be sufficiently thin to permit the weakened area to be piercable by a standard needle without the needle being substantially deformed. As will be discussed more fully below, this weakened area provides access to a fluid contained within vial 30. In a preferred embodiment, the weakened area is an inward facing dimple or indentation as shown. This feature can be formed in whole or part by drilling-out a part of the first end or by stretching the wall inwards while that portion of the vial is molten, e.g., during a molding process. Other suitable fabrication techniques will also be known to those of skill in the art.

The specific predetermined thickness depends upon the sale of the vial 30, the material it is formed from, and the type of needle which the vial 30 is designed to be pierced with. The material should be thick enough to prevent unwanted breakage but not so thick that the weakened area is unnecessarily hard to puncture with a needle. Some flexing and bending of the needle when piercing the weakened area 40 of the vial 3 is expected and normal. This minor deformation can result from slight misalignments of the needle from the piercing axis. However, the weakened area should be piercable without having to apply a pressure which would substantially deform the needle to the point of causing damage, such as a permanent bend or buckling of the needle wall.

Figure 5:
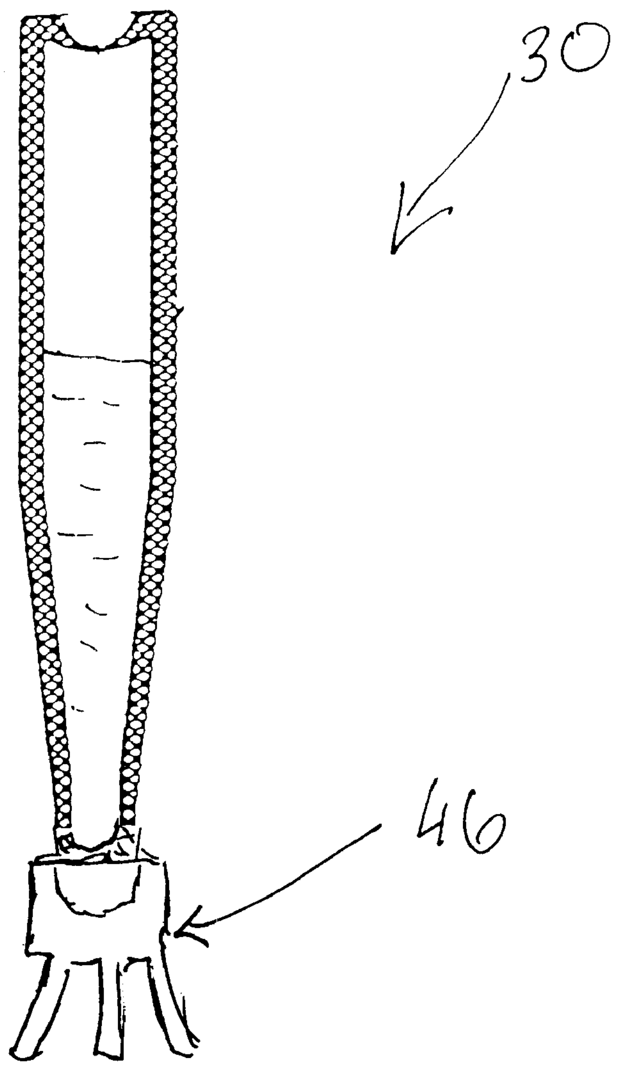
FIG. 5 is a side view if the vial of FIG. 4 fitted with an elastic spacer.
Figure 6:
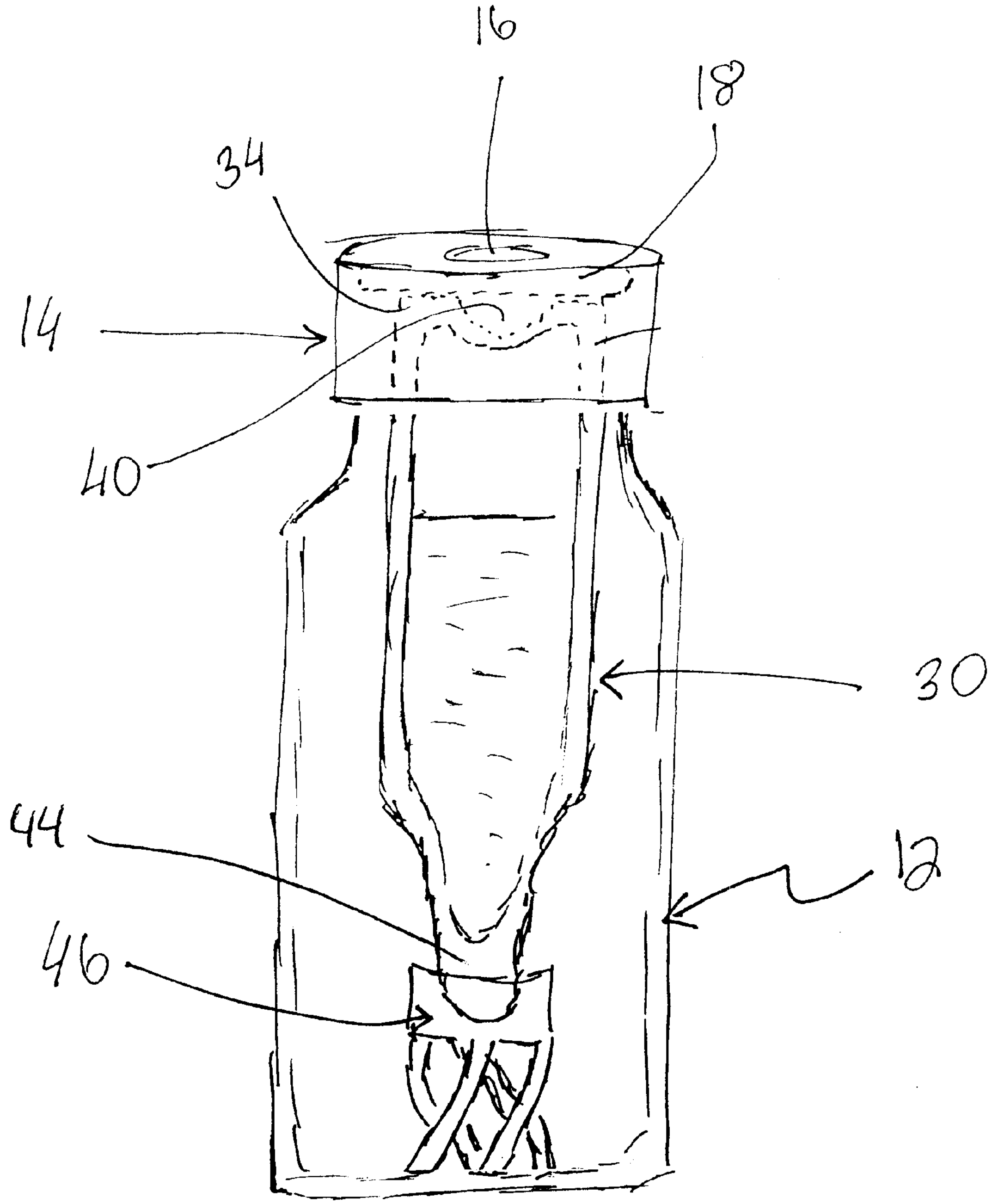
FIG. 6 is a side view of an autosampler jar containing the vial of FIG. 5.

Turning to FIGS. 5 and 6, once the vial 30 is filled and sealed, it can be distributed for subsequent use. In one implementation, the vial 30 is sized to be placed within a conventional autosampler jar 12. The vial is positioned so that the first end 34 is up. When the jar is closed, the weakened area 40 is adjacent the elastomeric closure 18 and generally aligned with the portion 16 of the jar lid 14 which is designed to be pierced by the needle. As will be appreciated, when a needle is inserted into the vial, the needle will subsequently pierce the weakened area 40 of the vial and thereby gain access to the fluid contained therein. Advantageously, the weakened area is centered within a generally conical or bowl shaped area as shown so that a needle hitting the first end of the vial is guided towards a central weakest area.

Preferably, an elastic spacer 46 is positioned on the second end of the vial 30. The spacer 46 protects the second end of the vial 30 from damage. It also can provide an elastic force which pushes the vial 30 upwards into the cap to keep the first end of the vial in contact with the elastomeric closure. The spacer 46 can be added by the user as needed or distributed already attached to the sealed vial.

In one embodiment, the vial 30 is formed from a soft glass which is relatively easy to melt and is designed to be pierced with standard stainless steel needles suitable for conventional chemical analysis or medical usage. Needles of this type generally have diameters in the range of about 0.03 inches to about 0.08 inches (e.g., from about 22 gauge to 33 gauge). For these needles, it has been found that for a vial sized generally as shown in FIG. 3*b* and formed of a conventional glass, a weakened area having a thickness ranging from between about 0.003 inches to 0.013 inches provides an acceptable balance between structural integrity and piercability. Most preferably, the thickness range is between 0.003 and 0.005 inches.

Based upon experimental results, a glass vial having a weakened area with a thickness nominally within the broader range has a breakage pressure ranging between about 1860 psi to 10,225 psi with the mean pressure equal to about 4800 psi. Because the tip of even a large needle covers a very small area, even very high relative pressures can be easily applied. For example, using a needle with a tip diameter of about 0.01 inches, this range of pressures can be generated using a force of only between about 8 ounces and 44 ounces. As will be appreciated, the particular optimal predetermined thickness range depends on the hardness and breaking characteristics of the vial material as well as the type of needle which is expected to be used. Thus, while the specific ranges discussed above are suitable for the preferred implementation, other ranges may be more appropriate for different configurations.

Figure 7:
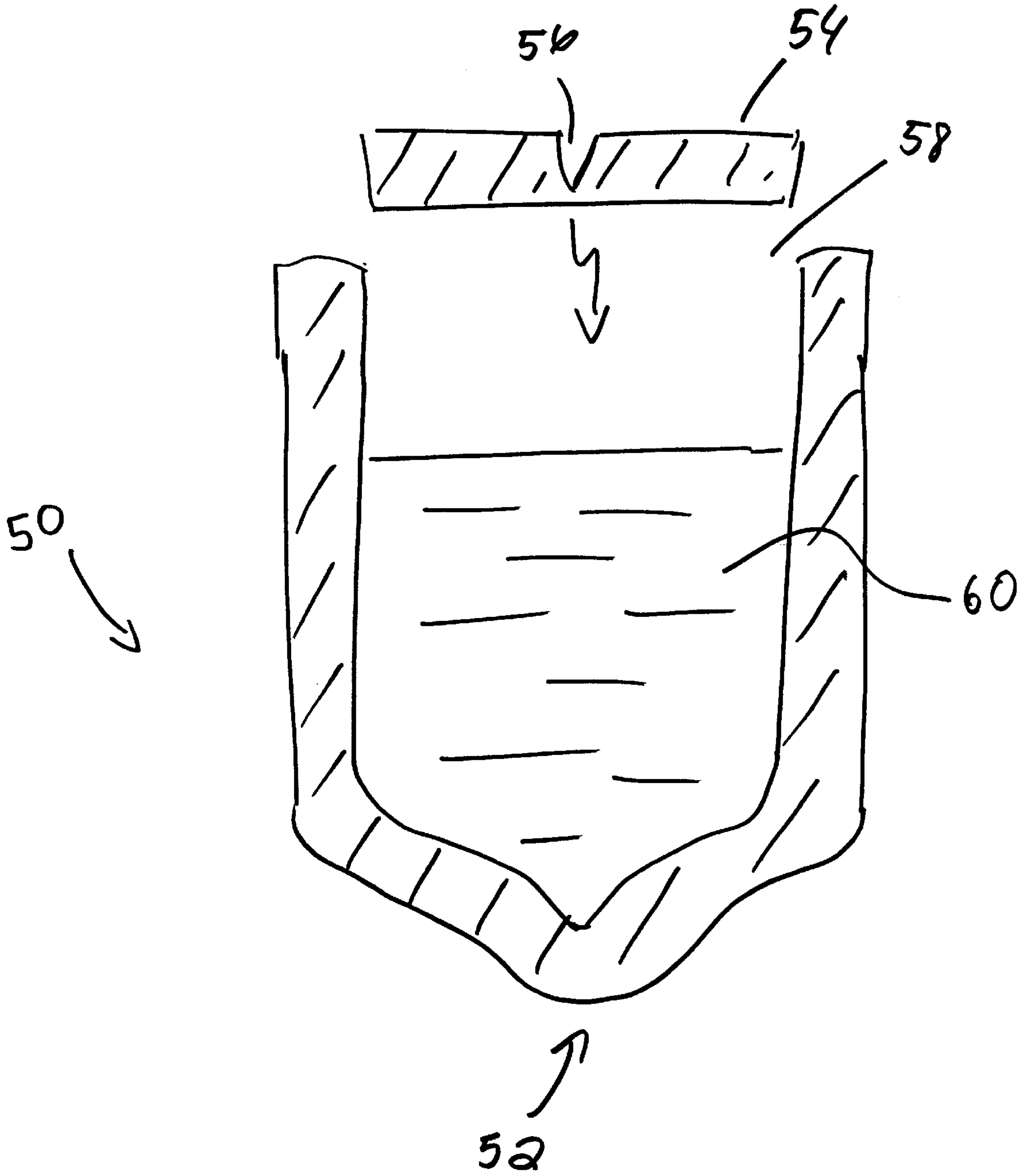
FIG. 7 is a side view of an alternative embodiment for an injectable vial.

Turning to FIG. 7, there is shown an alternative embodiment of a vial 50. The vial 50 is formed with a sealed end 52 and an open end 58. After the vial 50 is filled with fluid 60, the vial is sealed using an inert 54, such as a glass insert, which is placed within the open end of the vial and secured in place by, e.g., melting the glass around the rim, using adhesive, or even a friction fit. The weakened area can be formed as discussed above. Alternatively, the weakened area can be formed by forming one or more notches 56 in the insert either before or after the vial is sealed. Other variations are also possible. For example, the vial of FIG. 3*a* could be formed with a flattened first end 34 and the weakened area formed by scoring or notching the end in a manner similar to the weakened insert.

Another design aspect to consider is the size of any pieces of the vial 30 which may fall into the fluid when the weakened area 40 is pierced by a needle. Based on experimental testing of vials designed according to the specific most preferred parameters discussed above, the size of glass particles which fall into the contained fluid is distributed from between about 2 microns to 20 microns with a mean particle size of about 5 microns. Thus, the weakened area remains substantially intact during the piercing and removing operation. In general, the particles have no effect on the sample because differences in density between the glass particles and the fluid result in rapid settling of the particles to the bottom of the vial. Although there is a slight possibility of the particles being aspirated into the needle, such particles can easily be removed through the use of a conventional sub-micron syringe filter.

To further reduce the likelihood of particles entering the liquid, a film, such as a polymer film of suitable low molecular weight like polyolefin polymer (e.g., polyethylene), can be applied over the weakened part of the vial. The film (not shown) can be applied to the vial using various techniques known to those of skill in the art, including vapor deposition or application of a suitable liquid polymer solution. When the vial is subsequently pierced by a needle, the film will adhere to the fragmented particles and prevent them from falling into the enclosed liquid.

While the invention has been particularly shown and described with reference to preferred embodiments thereof, it will be understood by those skilled in the art that various changes in form and details may be made therein without departing from the spirit and scope of the invention.

What is claimed is:

1. An injectable jar containing a fluid therein comprising:

a jar having an open mouth and a bottom;

a cap fitted on the mouth;

an elastomeric closure situated between the cap and the mouth; the cap having an opening therein to expose a portion of the elastomeric closure;

a vial comprising a generally tubular glass body having sealed first and second ends and containing the fluid therein;

the first end having a weakened area therein of a predetermined thickness, the predetermined thickness being sufficiently thin for permitting piercing of said weakened area by a hollow needle, the weakened area remaining substantially intact without the needle being substantially deformed and with only the interior of the glass body communicating through the interior of the needle for providing safe access to the fluid when contained in the vial;

the vial contained within the jar such that the weakened area is adjacent the elastomeric closure.

2. The jar of claim 1, wherein the first end is in contact with the closure.

3. The jar of claim 1, further comprising an elastic spacer between the bottom of the jar and the second end of the vial, the spacer exerting a pressure tending to keep the first end in contact with the closure.

4. The jar of claim 1 wherein the predetermined thickness is between approximately 0.003 inches and 0.013 inches.

5. The jar of claim 4, wherein the predetermined thickness is between approximately 0.003 inches and 0.005 inches.

6. The jar of claim 1, wherein the weakened area is in an inwardly facing dimple formed in the first end.

7. The jar of claim 1, wherein the weakened area comprises at least one notch formed in the first end.

8. The jar of claim 1, wherein the first end comprises a glass insert contained within the body and having the weakened area formed thereon.

9. The jar of claim 1, further comprising a film covering the weakened area.

10. The jar of claim 9, wherein the film comprises a polyolefin polymer.

11. A method for providing fluids for extraction by a hollow needle comprising the steps of:

providing a vial comprising a generally tubular glass body having sealed first and second ends and containing the fluid therein, the first end having a weakened area of a predetermined thickness formed therein, the predetermined thickness being sufficiently thin to for permitting piercing of said weakened area by the needle, the weakened area remaining substantially intact without the needle being substantially deformed and with the interior of the glass body communicating through the interior of the needle for providing safe access to the fluid contained in the vial;

placing the vial inside of a jar having an open mouth and a bottom such that the first end of the vial is adjacent the mouth; and sealing the jar using a cap having an elastomeric closure, the cap having an opening which exposes a portion of the elastomeric closure.

12. The method of claim 1, further comprising the step of placing an elastic spacer between the second end of the vial and the bottom of the jar prior to sealing the jar, the elastic spacer providing a pressure tending to keep the first end in contact with the closure.

13. An injectable vial for storing a fluid comprising:

a glass body having a sealed first end and an open second end;

the first end having a weakened area therein of a predetermined thickness, the predetermined thickness being sufficiently thin for permitting piercing of said weakened area by a hollow needle, the weakened area remaining substantially intact without the needle being substantially deformed and with the interior of the glass body communicating through the interior of the needle for providing safe access to the fluid when contained in the vial.

14. The vial of claim 13, wherein the predetermined thickness is between approximately 0.003 inches and 0.013 inches.

15. The vial of claim 14, wherein the predetermined thickness is between approximately 0.003 inches and 0.005 inches.

16. The vial of claim 13, wherein the weakened area is in an inwardly facing dimple formed in the first end.

17. The vial of claim 13, wherein the weakened area comprises at least one notch formed in the first end.

18. The vial of claim 17, wherein the notch is generally conical.

19. The vial of claim 13, further comprising a film covering the weakened area.

20. The vial of claim 19, wherein the film comprises a polyolefin polymer.

* * * * *